United States Patent
Fose et al.

[11] Patent Number: 5,827,744
[45] Date of Patent: Oct. 27, 1998

[54] METHOD AND APPARATUS FOR CLEANING A LIQUID DISPENSING PROBE

[75] Inventors: James Brian Fose, Bear; Ching-Cherng Lee; John Paul Mizzer, both of Newark, all of Del.

[73] Assignee: Dade International Inc., Deerfield, Ill.

[21] Appl. No.: 893,634

[22] Filed: Jul. 11, 1997

Related U.S. Application Data

[63] Continuation of Ser. No. 553,939, Nov. 6, 1995, abandoned.

[51] Int. Cl.$^6$ .................. B08B 3/04; B08B 9/02
[52] U.S. Cl. .............. 436/49; 436/54; 422/100; 134/21; 134/22.11; 134/22.12; 134/170; 73/864.11; 73/864.22; 73/864.34
[58] Field of Search ................. 422/63, 67, 100, 422/99; 436/43, 47, 54; 134/170, 21, 22.11, 22.12; 73/864.11, 864.22, 864.24, 864.34

[56] References Cited

U.S. PATENT DOCUMENTS

| | | |
|---|---|---|
| 3,552,212 | 1/1971 | Ohlin ........................................ 73/423 |
| 3,964,526 | 6/1976 | Sindermann ............................. 141/1 R |
| 4,318,885 | 3/1982 | Suzuki et al. ............................. 422/68 |
| 4,323,537 | 4/1982 | Mody ........................................ 422/63 |
| 4,328,185 | 5/1982 | Reasons et al. .......................... 422/82 |
| 4,457,184 | 7/1984 | Shiono ................................. 73/864.11 |
| 4,516,437 | 5/1985 | Pedroso et al. ...................... 73/864.22 |
| 4,820,497 | 4/1989 | Howell ..................................... 422/63 |
| 5,133,373 | 7/1992 | Hoffman et al. ......................... 134/88 |
| 5,186,194 | 2/1993 | Kitajima ................................. 134/154 |
| 5,279,794 | 1/1994 | Sasao ..................................... 422/100 |
| 5,408,891 | 4/1995 | Barber et al. ........................ 73/864.22 |

*Primary Examiner*—Long V. Le
*Attorney, Agent, or Firm*—Leland K. Jordan

[57] ABSTRACT

A method for cleaning a liquid sample probe in which the probe is positioned within a washing chamber inside a wash body and a purging liquid solution is pumped through the probe into the chamber. A cleaning liquid solution may also be pumped into the chamber around the probe. Either or both liquids are subsequently vacuumed from the chamber drawing air through an annular gap between the probe and the wash body thereby creating a cleaning air flow between the exterior probe surface and the wash body. The cleaning air flow removes all cleaning liquid solution and/or purging liquid solution as the probe is removed from the wash body.

12 Claims, 5 Drawing Sheets

METHOD AND APPARATUS FOR CLEANING A LIQUID DISPENSING PROBE

This is a continuation of application Ser. No. 08/553,939, filed on Nov. 6, 1995, now abandoned.

BACKGROUND OF THE INVENTION

1. Field of the Invention

The present invention is related to the field of liquid probes and more particularly to a method and apparatus for cleaning liquid sample probes. Although not limited to the field of automated clinical analyzers, the present invention is particularly useful when applied therein.

2. Description of The Prior Art

Automated clinical chemistry analyzers are well known in the art and generally use an aspirating means such as a sampling tip, or probe or needle, to transfer predetermined volumes of liquid samples or liquid reagents between receptacles, such as sample containers, reagent containers and reaction cuvettes disposed at various locations on the analyzer. The aspirating means, hereinafter referred to as a sample probe, is typically an elongated, needle-like member having a hollow passage whereby liquid may be drawn into and dispensed from the sample probe using appropriate pumping resources. Such sample probes may be used to aspirate and deliver liquid samples or one or more liquid reagents between receptacles, e.g., from containers to one or more reaction cuvettes, where a chemical analysis of the sample is conducted, either with the same sample probe or with one or more liquid sample probes.

A common problem in such aspirating means is the risk of liquid "adhesion" and/or "carryover". Carryover occurs when a probe having residual traces of a previously dispensed sample or reagent is introduced into volume of a different reagent or sample. Carryover is usually manifested as the contamination of a given reagent supply or a given sample volume by the introduction thereinto of other reagents or samples that remain on or in or are adsorbed by the sample probe. Adhesion occurs when a portion of an aspirated reagent or sample adheres to the exterior surface of a sample probe and is not appropriately removed therefrom.

To minimize adhesion and/or carryover, the sample probe is generally cleaned by washing prior to subsequent operations. Washing is typically accomplished by lowering the sample probe into a cleaning resource that contains an appropriate cleaning liquid solution. The cleaning liquid solution washes the exterior of the sample probe. The interior of the sample probe is cleaned by aspirating and discharging the cleaning solution. Alternatively, the sample probe may be cleaned by discharging a purge liquid through the sample probe into a drain. Washing may use a jet of drying air forced under pressure through the sample probe or at the exterior surface thereof. In this manner the volume of residual carryover on the exterior surface or the interior of the sample probe is minimized. As a practical matter, cleaning of both the sample probe and cleaning resource is required to preserve proper operation.

Analysis instruments having a typical sample probe wash station are described in U.S. Pat. No. 3,964,526 (Sindermann), U.S. Pat. No. 4,318,885 (Suzuki et al.) and U.S. Pat. No. 3,552,212 (Ohlin), and U.S. Pat. No. 4,323,537 (Mody). A common problem with sample probe washing, however, is residual liquid or contaminants may be adsorbed on the sample probe despite washing. This residue may mix with subsequent samples or reagents drawn into the sample probe and can result in the introduction of a contaminated sample or reagent. Furthermore, the presence of additional residual droplets of sample or reagent on the exterior or interior of the sample probe may cause unwanted additional liquid to be introduced into a destination receptacle. This unwanted residue may mix with subsequent sample or reagents drawn into the sample probe and interfere with chemical analyses. Sample probe cleaning is a particularly troublesome problem when exacerbated by the trend to smaller and smaller sample volumes. A minute volume of cleaning liquid solution may remain within or on the exterior surface of a sample probe causing a corresponding deficiency in the volume of sample liquid later transferred to a reaction vessel. Such a sample volume deficiency may create serious analytical errors in automated assays for calcium, magnesium and glucose, in particular.

U.S. Pat. No. 5,297,794 (Sasao) addresses this problem by using flushing water in combination with an inclined waterway channel in which the sample probe is immersed. As the sample probe traverses the waterway channel, it is withdrawn and liquid communication between the waterway and the sample probe is broken and cleaning ceases, leaving liquid droplets on the sample probe.

U.S. Pat. No. 5,408,891 (Barber et al.) also addresses this problem and used a wash collar with (1) pressurized water supplied through the inner bore of a fluid sample probe to wash the inside of the sample probe, and (2) a separate supply of water washing the sample probe and the exterior of the sample probe when positioned in a small central chamber within the wash collar. The wash collar is of complex design including five differently shaped portions through a central bore in which the sample probe moves. The water is drawn away from the sample probe and out of the wash collar through a vacuum port located in the lower portion of the bore and in communication with a vacuum source. Unfortunately, only a small portion of external air enters the wash collar from the direction of sample probe insertion, the majority coming from an enlarged lowermost portion of the wash collar bore. This does not permit thorough cleaning of the sample probe.

It is believed to be advantageous to provide a cleaning method which effectively eliminates extraneous material from the full interior and the full exterior of the sample probe while at the same time not unduly adding to the complexity of washing resources nor detracting from the throughput of the instrument.

SUMMARY OF THE INVENTION

Many of these prior art deficiencies are reduced with the present invention which relates to a method for cleaning a liquid sample probe, the sample probe having an interior hollow portion and an exterior surface, the hollow portion in communication with a resource of a washing purging liquid solution. The sample probe is moveable into and out of a closed bottom bore within a wash body, the bore being sized to define an annular gap between the exterior surface of the sample probe and an inside dimension of the bore. The wash body has at least one vacuum port connected to a vacuum resource and at least one liquid port connected to a wash liquid solution resource, the vacuum and liquid ports being in communication with said bore.

Cleaning the probe comprises positioning the sample probe within the bore and pumping wash liquid solution into the bore and vacuuming the cleaning liquid solution from the upper portion of the bore. As a result of said vacuuming, air is drawn through said annular gap so that a cleaning air flow from outside the wash probe is created between the exterior sample probe surface and the bore, when removing the sample probe from the wash body, the cleaning air flow being effective in removing cleaning liquid solution from the exterior surface of the sample probe. In an alternate embodiment, a wash or purging liquid solution is pumped through the hollow portion of the sample probe into the bore before cleaning liquid solution is pumped into the bore.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
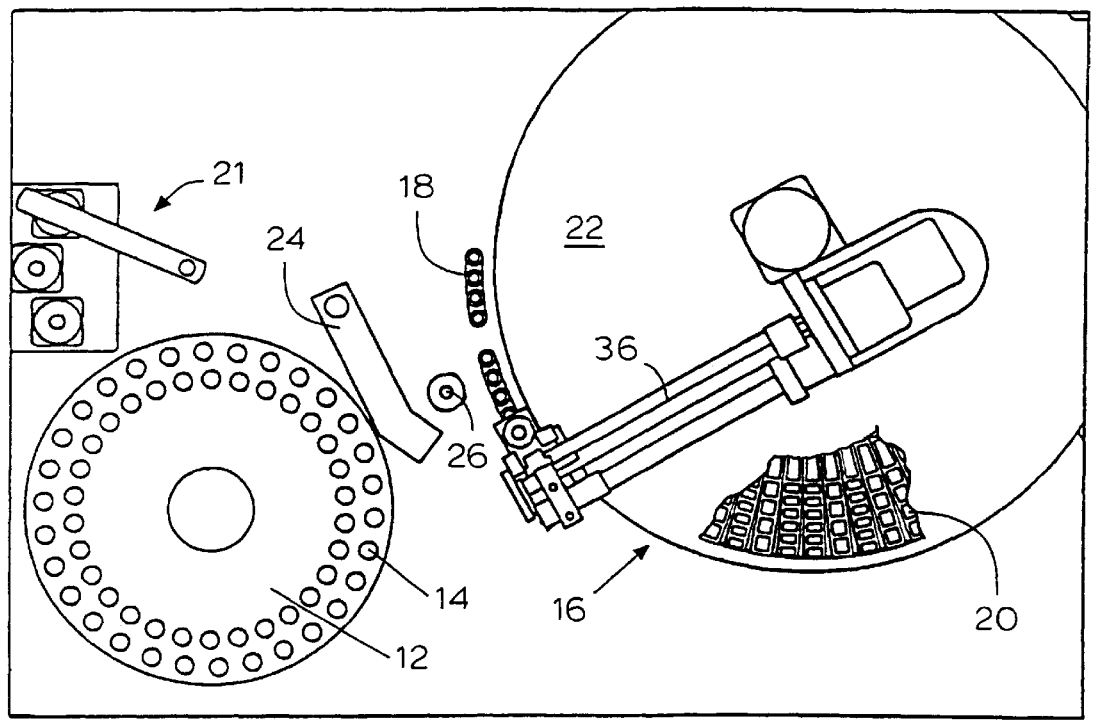
FIG. 1 is a schematic diagram of an automated analyzer in which the present invention may be used to advantage.

FIG. 1 shows schematically the elements of a conventional automatic chemical analyzer, such as the DIMENSION™ (sold by E. I. du Pont de Nemours and Company) comprising a sample carousel 12 used to support a plurality of sample containers 14, a reaction vessel or cuvette carousel 16 adapted to receive a plurality of reaction cuvettes 18 and reagents from reagent cartridges 20 illustrated as disposed beneath a cut out portion of a lid 22 which covers various thermally controlled areas during operation. A secondary analytical module 21 operating independently of the reaction cuvettes 18 may be present in the analyzer. Reagent cartridges 20 are preferably a multi-compartmented container such as those sold under the tradename FLEX™ by E. I. du Pont de Nemours and Co., Inc., Wilmington, DE. Reaction cuvettes 18 are formed by pulling two different composition ribbons of clear film from a cuvette film cartridge, not shown, onto the periphery of the cuvette carousel 16. The cuvette carousel 16, preferably in the form of a wheel, has about 100 separate cuvette cavities. The inner wall of each cavity has an inner wall to allow transmission of light. There is a cuvette forming station, not shown, in which a clear plastic film ribbon is heat softened, molded onto the inner wall of the cuvette or reaction vessel cavity and its optical window. The cuvette carousel 16 is then rotated to stretch the outer clear plastic film ribbon across the molded inner film and the two are heat-bonded to each other. A small opening remains at the top of the cuvette 18 to allow the addition of reagent and sample. A rotatable sample arm 24 and wash resource 26, constructed in accordance with this invention, and described in more detail hereinafter, are located proximate the sample carousel 12 and cuvette carousel 16.

Figure 2:
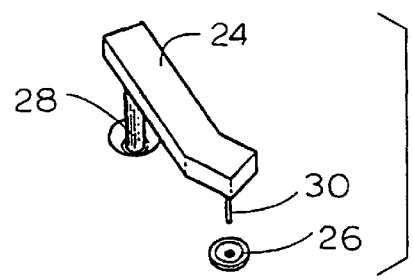
FIG. 2 is a perspective view of the sample probe and wash resource of FIG. 1.
Figure 3:
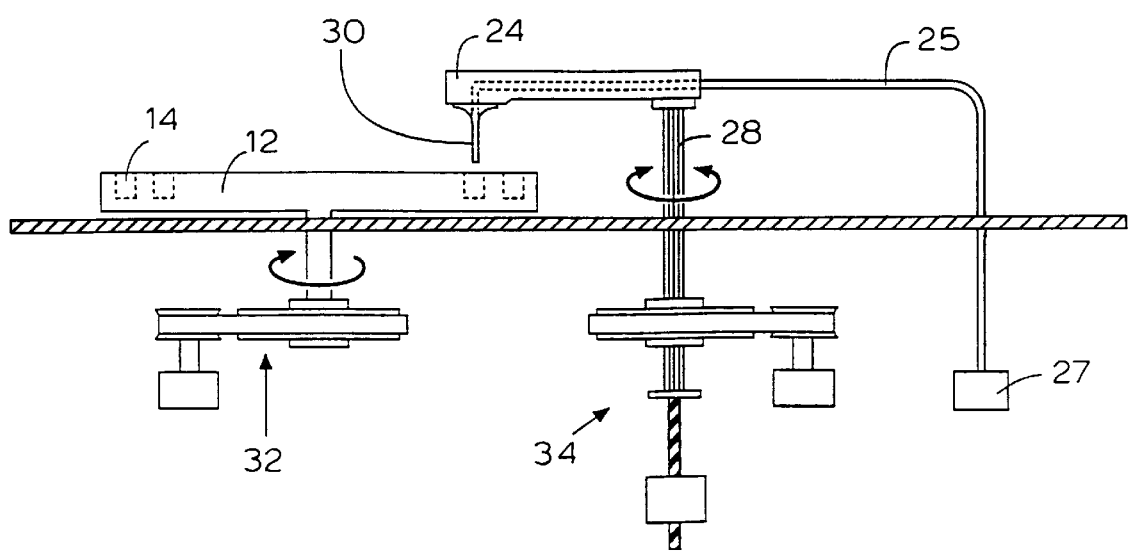
FIG. 3 is a side elevational view of a portion of the automated analyzer of FIG. 1.

FIG. 2 shows the sample arm 24 mounted to a rotatable shaft 28 (FIG. 3) so that, taken with FIG. 1, movement of a sample arm 24 describes an arc intersecting all three components 12, 16, and 26 enabling a hollow, liquid-carrying sample probe 30, supported by sample arm 24 and adapted to aspirate and discharge liquids, to conduct the following four activities: sample aspirate from a sample container 14, wash of the external surface of the probe, sample dispense into a cuvette 18, and discharge and wash at wash resource 26. FIG. 3 shows a conventional rotational drive mechanism 32 adapted to rotate the sample carousel 12 and another conventional rotational and vertical drive mechanism 34 adapted to rotate and vertically translate sample arm 24 in order to bring a required sample container 14 into alignment with sample probe 30.

Referring again to FIG. 1, a reagent arm 36 of conventional design draws reagent from an appropriate reagent cartridge 20 and deposits reagent within a predetermined reaction cuvette 18 and ultrasonically mixes the reagent and chase water. Rotatable sample arm 24 draws sample from an appropriate sample container 14, positions the sample probe 30 with the wash resource 26 for cleaning, and deposits the sample within the predetermined reaction cuvette 18. The rotatable sample arm 24 then is positioned within wash resource 26 where the sample probe 30 is cleaned. Photometic analyzing means, not shown, located beneath the cuvette carousel 16 measures light absorbance through the cuvette 18 at various wavelengths. The photometic analyzing means is of conventional design and includes a photometer and a source lamp that emits a light beam which passes through various lens housed in a rotatable detector arm to a photodetector which, being mounted on the outer-end of the detector arm adjacent the outer periphery of the cuvettes 18, rotates about the cuvette carousel 16. The photodetector relays absorbance readings through the computer where the readings are converted into concentration units. A conventional computer using a microprocessor is used to control the various components of the analyzer and to store system parameter changes and test results. After sample probe 30 is withdrawn from cuvette 18, the sample probe 30 is repositioned within the wash resource 26, more specifically a wash body (FIG. 5) as will be described, where a wash liquid such as a cleaning liquid solution is pumped through hollow portion of the sample probe 30 and a similar wash liquid, designated as a purging solution, is pumped around the exterior surface of the sample probe 30. Subsequently, the sample arm 24 is raised to displace the sample probe 30 from the wash resource. According to the present invention, the annular gap between the sample probe 30 and the bore 60 of the wash body 40 is sized so that the air flow induced therethrough by the vacuum source applied to the upper portion of the bore 60 (FIG. 5) is effective in cleaning the sample probe 30, thereby reducing the possibility of diluting or otherwise contaminating a subsequent sample.

A key feature of the present invention is the method of washing a sample probe 30 so as to simultaneously achieve increased precision of sample volume delivery into a reaction cuvette as well as reduction of routine maintenance of wash resource 26 and sample probe 30. As used herein, the term "washing" should be considered as potentially including pumping of a purging liquid solution through the hollow portion of the sample probe 30, rinsing the exterior surface of sample probe 30 with a wash liquid solution, repeated aspirations of a wash liquid solution into and out of the sample probe 30 to flush it and vacuuming a wash liquid from the sample probe 30.

Figure 4:
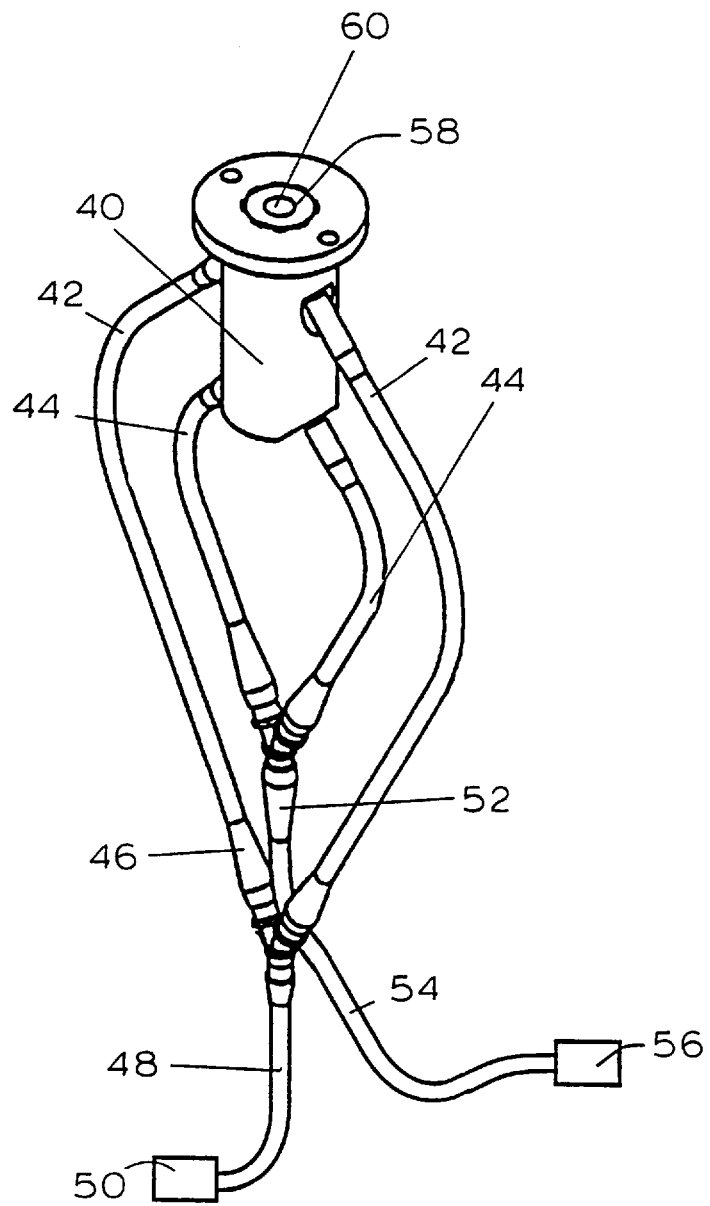
FIG. 4 is a perspective view of the wash resource of FIG. 1.

FIG. 4 shows wash resource 26 constructed in accordance with a preferred embodiment comprises a wash body 40 having a pair of vacuum tubings 42 ported thereto through a first pair of ports 62 (FIG. 5) formed through the upper portion of wall of wash body 40 and another pair of cleaning liquid solution tubings 44 also ported thereto through a second pair of ports 64 (FIG. 5) formed through the lower portion of the wall of wash body 40. The ported vacuum tubings 42 are joined by a suitable fitting 46 to a length of tubing 48 which is in turn connected to a controllable vacuum source or vacuum means 50. Likewise, wash or cleaning liquid solution tubings 44 are joined by a suitable fitting 52 to a length of tubing 54 which is in turn connected to a wash cleaning liquid solution source 56. Tubings 42 and 44 may be ported or joined to the wash body 40 using conventional means; however, preferably, use of barbed port-tubing connections throughout wash body 40 has the advantage of making it unlikely that the tubings will be inadvertently dislodged.

Figure 5:
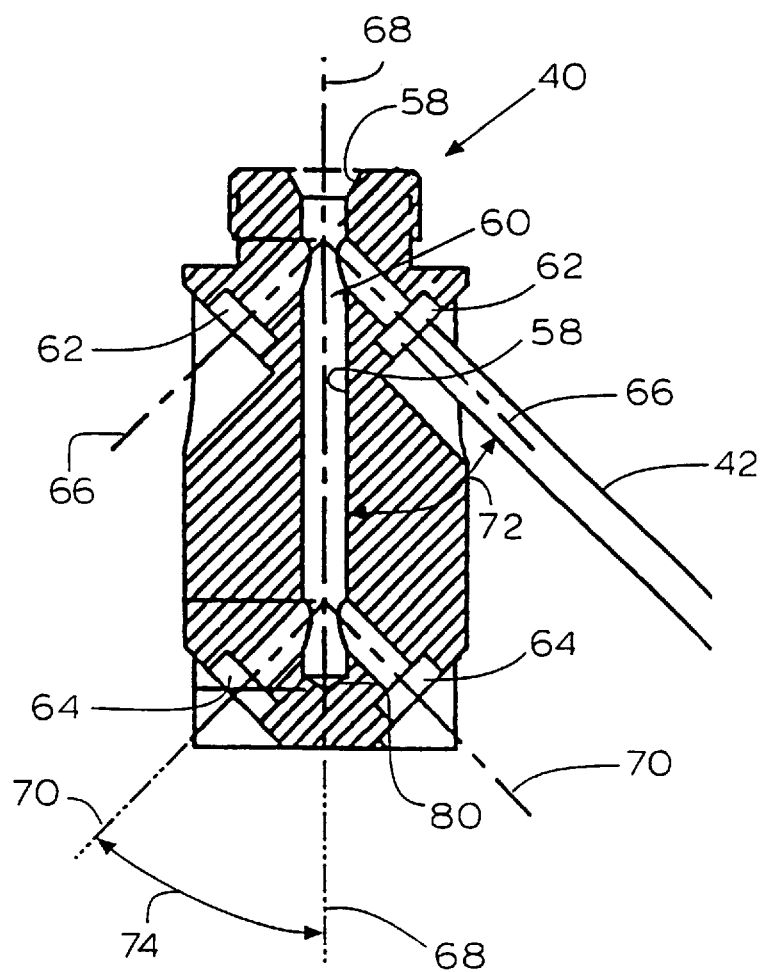
FIG. 5 is a cross section view of a portion of the wash resource of FIG. 4; and, FIG. 6 is a simplified cross section of a portion of the wash resource of FIG. 4

FIG. 5 shows the wash body 26 as having a vertically oriented bore defined by a generally circular, though not necessarily central bore 58 extending partially therethrough to form a well-like washing chamber 60 having a closed bottom, the chamber 60 being in vacuum and fluid communication with vacuum tubings 42 and wash liquid solution tubings 44 by means of the two pairs of diametrically opposed vacuum and fluid ports 62 and 64, respectively, located as described in the upper portion of the bore 58 to facilitate external airflow about the sample probe for cleaning, as will be described. The mechanism of vacuum communication in an alternate embodiment of the present invention comprises a single port 45 in place of the pair of ports 62 and in a second alternate embodiment, shown in FIG. 6, comprises an annular port 59 formed in the wash body around the central bore surface 58. In the alternate embodiment of the present invention, construction of the wash body 40 shown in FIG. 6 requires forming a wash body cap 41 to adapt to a wash body base 43 thereby creating said annular port 59. In this alternate embodiment, the annular port 59 and associated annular gap 61 having a dimension between 0.001 and 0.080 inches, preferably about 0.025 inches, between the sample probe 30 and the central bore surface 58 cooperate with vacuum means 50 to create the cleaning air flow effect between the exterior surface of the sample probe 30 and the bore 58.

Figure 6:
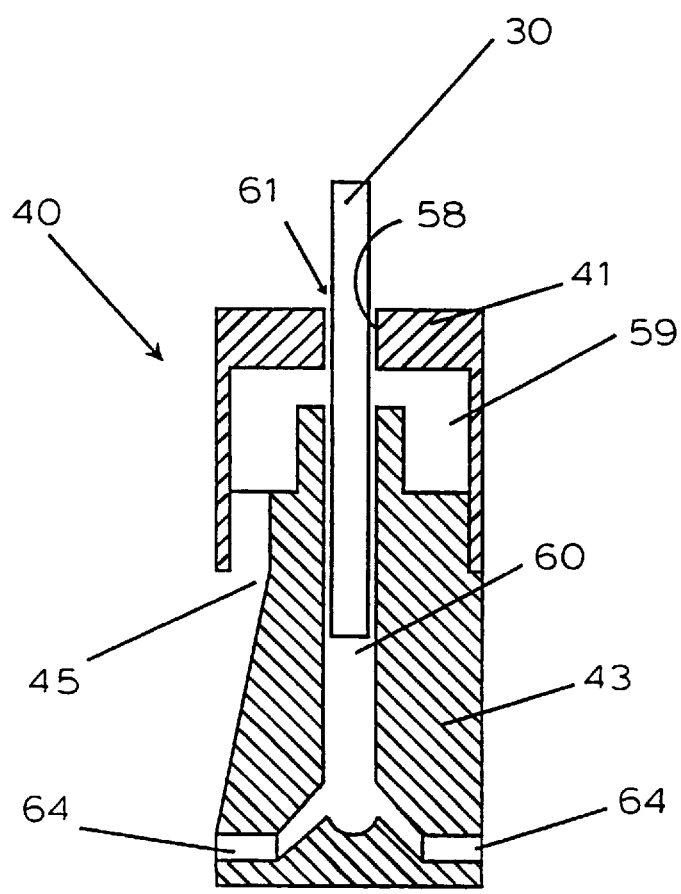

For simplicity of illustration in FIG. 5, only one tubing 42 is shown connected to wash body 40. Furthermore, for illustration purposes only, the very top portion of central bore surface 58 is shown in a countersunk fashion to facilitate insertion of the sample probe 30 into the wash body 40. In an alternate arrangement, the intersection of the wash body 40 and the central bore surface 58 form a right angle, as illustrated in FIG. 6. As previously described, vacuum means 50 is in vacuum communication with the vacuum ports 62 causing a vacuum to be created in the uppermost portion of the washing chamber 60 when vacuum means 50 is activated.

The angular separation 72 between the centerlines 66 of ports 62 and the centerline 68 of the chamber 60 has been determined as equally effective in creating the cleaning air flow of the present invention for angles between 0 and 90 degrees. Likewise, the angular separation 74 between the centerlines 70 of ports 64 and the centerline 68 of the chamber 60 is equally effective in introducing wash liquid of the present invention for angles between 0 and 90 degrees.

In all preferred embodiments, wash resource 26 is fabricated from a polycarbonate material, sold by General Electric Corporation under the trademark "Lexan" and the tubings are of a conventional silicon material. In one preferable application, the wash resource 26 has an external diameter between 0.5 and 1.0 inches, a height between 1.0 and 2.0 inches, the bore has a diameter between 0.1 and 0.2 inches and a depth between 1 and 1.25 inches. In this application, the centerlines 66 of each of the first pair of ports 62 are angled and the ports are located so that the centerlines 66 intersect the centerline 68 of the chamber 60 about 0.2 inches from the entrance of the washing chamber 60. The centerlines 70 of each of the second pair of ports 64 are angled and the ports 64 are located so that the centerlines 70 intersect the centerline 68 of the chamber 60 about 1.1 inches from the entrance of the washing chamber 60. The washing chamber 60 has a diameter in the range 0.051 to 0.200 inches, so that when a typical sample probe 30 has an external diameter in the range 0.050 to 0.120 inches, an annular gap having a dimension in the range 0.001 to 0.080 inches, preferably about 0.025 inches, is created between the sample probe 30 and the central bore surface 58.

Preferable wash liquids for the cleaning solutions include deionized water, detergent water, Clorox®, alcohol, and sodium hydroxide solution.

A method of the present invention for using the wash resource 26 of the present invention, described hereinafter in greater detail, includes inserting sample probe 30 to full immersion within the washing chamber 60 of the wash body 40, pumping wash liquid, referred to as a purging fluid, through and out of the sample probe 30 using purging liquid solution pumping means 27 (FIG. 3), pumping wash liquid, referred to as a cleaning liquid solution, through cleaning liquid solution tubings 44 (FIG. 4) and through ports 64 (FIG. 5) upwardly and around the exterior of the sample probe 30 using pumping means 56 (FIG. 4), applying a vacuum within the washing chamber 60 of the wash body 40 using vacuum means 50 (FIG. 4), deactivating the purging liquid solution pumping means 27, deactivating the cleaning liquid solution pumping means 56, removing sample probe 30 from immersion within the washing chamber 60 of the wash body 40 so as to create an annular cleaning air flow from outside the wash body 40, between the exterior sample probe 30 surface and an inner wall 58 of the washing chamber 60, and deactivating the vacuum means 50. This annular air flow is facilitated by the positioning of the vacuum inlet to the upper portion of the bore 58. Because of the introduction of purging liquid solution into the chamber 60, it is apparent that the cleaning liquid solution and the purging liquid solution may mix together so that the cleaning air flow acts on both liquids. These steps may be performed sequentially or may be performed to overlap one another. Deactivating the vacuum means 50 is an optional step in the washing process.

The operation of the wash resource 26 shown in the figures may be understood by reference to FIG. 2 through FIG. 5. In a typical instance sample probe 30 is axially positioned in alignment with the center line 68 of the washing chamber 60, lowered into the wash body 40 and a wash or cleaning liquid solution pumped through the tubings 44 and into the washing chamber 60, washing the exterior surface of the sample probe 30. Preferably the cleaning liquid solution is deionized water and is pumped into the washing chamber 60 at a flow rate in the range of 1 to 2 ml/sec. Simultaneously, previously, afterwards, or not at all, a wash or purging liquid solution may be caused to flow from a purging liquid solution reservoir through an appropriate tubing 25 (FIG. 3) using pumping means (both denoted by 27 on FIG. 3) and then through the sample probe 30. As the purging liquid solution exits the sample probe 30, it is directed downwardly in the washing chamber 60 where it strikes against the lower boundary 80 of the washing chamber 60. Preferably the purging solution liquid is also deionized water and is pumped through the sample probe 30 into the washing chamber 60 at a flow rate in the range of 1 to 2 ml/sec.

The wash liquids (purging liquid solution and/or the cleaning liquid solution) are thus caused to flow upwardly over the exterior surface of the sample probe 30 within the washing chamber 60 and toward an annular gap 61 defined between the sample probe 30 and the central bore surface 58. At this occurrence, or shortly thereafter, the sample probe arm 24 (and hence sample probe 30) is caused by motor 34 to be raised slowly out of the washing chamber 60, preferably at a rate in the range 5–60 cm/sec. At this occurrence, the vacuum means 50 is activated causing a vacuum to be created in accordance with this invention in the uppermost portion of the washing chamber 60. Since the chamber 60 is in liquid communication with atmospheric pressure (via the top portion of the annular gap 61 as best seen in FIG. 6), air is drawn therein with relatively high flow, creating a "cleaning air flow" between the exterior surface of the sample probe 30 and the bore wall 58 of the wash body 40. An important feature of the present invention is the discovery of this cleaning air flow as being superior in removing fluids from the exterior surface of the sample probe 30. It has been discovered that a vacuum force sufficient to create a flow of air in the range 3 to 10 liters/min is sufficient to create the cleaning air flow of the present invention that is effective in liquid from the exterior surface of the sample probe 30. As used herein, the term "effectively cleaning" should be considered as eliminating all but less than about 0.30 microliters of liquid from the exterior surface of the sample probe 30. It should be appreciated that as the annular gap between the sample probe 30 and the central bore surface 58 is increased, a corresponding increase in the force of the applied vacuum is necessitated. Similarly, if the rate of withdrawal of the sample probe 30 from the washing chamber 60 is increased, a corresponding increase in the force of the applied vacuum is necessitated to achieve the same cleaning air flow removal of superfluous fluids on the exterior surface of the sample probe 30. The washing process using the cleaning air flow method of the present invention is also effective in removing any aerosol generated proximate the wash resource during washing processes. This is particularly important during handling of hazardous biological samples.

The internal sample probe 30 wash and external sample probe 30 wash accomplished by the activation of pumping means 56 and 27 and vacuum means 50 may also be accomplished such that an overlap of the washing liquid flow times occurs. Thus, instead of the pumping means 27 deactivating before the pumping means 56 is activated, the pumping means 56 may first be activated to initiate the flow of external wash liquid and then the pumping means 27 may then be activated to initiate the flow of purging liquid solution. In either case, that is, where there is no overlap in time of the purging liquid solution flow from pumping means 27 and then from pumping means 56, or where there is such an overlap in time, the vacuum means 50 deactivates last, removing all liquids from around the outside length of the sample probe 30 as the sample probe 30 is removed from within the washing chamber 60 to thus finish the external cleaning of the sample probe 30. Optionally, vacuum means 50 may be left activated continuously to achieve the same purpose.

The wash resource 26 is operative to effect a first surprising result of thoroughly reducing carryover of the washing liquids whereby the accuracy of sample volume sensitive assays is increased. If an analyzer 10 is equipped with the wash resource of the present invention, it has been discovered that the cleaning air flow around the withdrawn sample probe 30 is effective in removing most superfluous washing solutions to the extent that less than 0.030 microliters of liquid remains on exterior surface of the sample probe 30. When the present invention is employed as described herein, variations in sample volume sensitive assays, most notably for calcium, magnesium and glucose, are reduced in the range 10–50% in the instance that sample volumes in the range 2 to 5 microliters are required in the assay.

The cleaning resource is operative to effect a second surprising result of reducing the frequency of maintenance cleaning. If an analyzer 10 is equipped with the wash resource of the present invention, it has been discovered that even more than 20,000 sample aspirations can occur before the necessity for maintenance cleaning. Prior to the use of the particular wash resource 26, maintenance cleaning was routinely scheduled in commercial installations after 3,000 sample aspirations. While the mechanism for this improved performance is not fully understood, it can be supposed that the feature of full immersion of the sample probe 30 within the washing chamber 60 during washing of the sample probe 30 is a contributing factor.

The combination of the vacuum removal of liquids from the washing chamber 60, coupled with the withdrawal of the sample probe 30 from the washing chamber 60, permits thorough cleaning of the sample probe 30 while increasing the efficiency of the analyzer 10 by minimizing the time necessary for maintenance cleaning. Those skilled in the art, having the benefit of the teachings of the present invention as hereinabove set forth may effect numerous modifications thereto. It should be understood that these and other modifications lie within the scope of the present invention as set forth in the appended claims.

What is claimed is:

1. A method of cleaning a liquid sample probe using a wash body having an upper portion and lower portion with a bore closed at the lower portion, the wash body adapted to receive said sample probe thereby defining an annular gap between said bore and said sample probe, comprising the steps of:

introducing said sample probe into said bore;

applying a wash liquid to the lower portion of said bore; and, withdrawing said sample probe from said bore while subjecting the upper portion of said bore to a vacuum, thereby to create a flow of air only through the annular gap to clean only the exterior portion of the sample probe.

2. The method of claim 1 which includes the step of passing a purging liquid through the sample probe prior to applying said wash liquid.

3. The method of claim 2 which includes the step of discontinuing said purging liquid after applying said wash liquid.

4. The method of claim 3 which includes the step of discontinuing the flow of wash liquid before subjecting the bore to a vacuum.

5. A method of claim 1 which includes the step of withdrawing the sample probe from the bore at the rate of 4 to 25 inches per second.

6. The method of claim 1 which includes sizing the sample probe and the bore to define an annular gap there between in the range of between 0.001 and 0.08 inches.

7. An apparatus for cleaning a liquid sample probe having an exterior surface, the apparatus comprising:

a wash body having a central bore with a closed bottom, the bore sized to permit a flow of air through an annular gap defined between the sample probe and the bore, the sample probe being moveable into and out of said bore;

means for introducing a cleaning liquid into a lower portion of said bore;

a source of vacuum connected to an upper portion of said bore; and, means to apply vacuum from the source of vacuum when removing the probe from the wash body so that the flow of air only through the annular gap is effective in removing cleaning liquid from only the exterior surface of the sample probe.

8. The apparatus of claim 7 wherein the annular gap is sized in dimension so that vacuum liquid from said bore and simultaneously drawing air through said annular gap generates an air flow in the range 3 to 10 liters per minute.

9. The apparatus of claim 7 wherein the annular gap is in the range between 0.001 and 0.080 inches.

10. The apparatus of claim 7 wherein the vacuum source is in communication with the bore by a single port.

11. The apparatus of claim 7 wherein the wash body defines an annular region in its upper portion in communication with the exterior surface of the sample probe, said annular region being in communication with the vacuum source.

12. The apparatus of claim 7 which includes means for withdrawing the sample probe from the wash body at a rate in the range between 4 and 25 inches per second.

* * * * *